(12) United States Patent
Nizza et al.

(10) Patent No.: US 9,709,533 B2
(45) Date of Patent: Jul. 18, 2017

(54) METHOD AND CIRCUIT FOR DETERMINING RESONANT FREQUENCIES OF A RESONANT DEVICE

(71) Applicant: STMicroelectronics S.r.l., Agrate Brianza (IT)

(72) Inventors: Nicolo Nizza, Marsala (IT); Paolo Pascale, Rho (IT); Andrea Diruzza, Roccasecca (IT); Michele Berto Boscolo, Sottomarina (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 368 days.

(21) Appl. No.: 13/721,721

(22) Filed: Dec. 20, 2012

(65) Prior Publication Data
US 2013/0167643 A1    Jul. 4, 2013

(30) Foreign Application Priority Data

Dec. 29, 2011   (IT) .......................... MI2011A002421

(51) Int. Cl.
| | | |
|---|---|---|
| *G01H 11/00* | (2006.01) | |
| *G01N 29/36* | (2006.01) | |
| *G01H 13/00* | (2006.01) | |

(52) U.S. Cl.
CPC ............ *G01N 29/36* (2013.01); *G01H 11/00* (2013.01); *G01H 13/00* (2013.01)

(58) Field of Classification Search
CPC ........ G01N 29/36; G01N 29/12; G01H 13/00; G01H 11/00; G01H 11/06; G01H 11/08; G01K 11/04; G01M 7/08; G01M 13/045; G01M 13/028; G01M 15/12

USPC .............. 324/76.52, 727, 652; 73/1.82, 579, 73/514.34, 35.09, 35.11, 593, 587, 651
See application file for complete search history.

(56) References Cited

U.S. PATENT DOCUMENTS

| | | | |
|---|---|---|---|
| 3,374,663 A | 3/1968 | Morris | |
| 4,015,202 A | 3/1977 | Fredriksson et al. | |
| 4,201,077 A * | 5/1980 | Froidevaux | G04D 7/1214 |
| | | | 324/76.52 |
| 5,414,406 A * | 5/1995 | Baxter | G08B 3/10 |
| | | | 116/142 R |
| 7,053,798 B2 * | 5/2006 | Popineau | G06F 3/038 |
| | | | 341/20 |
| 8,132,459 B2 * | 3/2012 | Toga | G01P 21/00 |
| | | | 73/514.34 |

(Continued)

FOREIGN PATENT DOCUMENTS

SU            832352 A1    5/1981

*Primary Examiner* — Michael A Lyons
*Assistant Examiner* — Suman K Nath
(74) *Attorney, Agent, or Firm* — Seed Intellectual Property Law Group LLP

(57) ABSTRACT

A method determines a resonance frequency of a resonant device. The method includes stimulating the resonant device with a periodic input signal having a frequency in a frequency interval; determining a frequency value for said periodic input signal in said frequency interval for which a phase-difference between said periodic input signal and a corresponding periodic output signal of the resonant device is minimum; generating a flag indicating that a resonance frequency has been determined; and generating signals representing said resonance frequency as a value of the frequency of said periodic input signal.

21 Claims, 16 Drawing Sheets

(56) References Cited

U.S. PATENT DOCUMENTS

| | | | |
|---|---|---|---|
| 2003/0151400 A1* | 8/2003 | Petrovich | G01D 3/06 324/76.52 |
| 2010/0064809 A1 | 3/2010 | Toga et al. | |
| 2010/0198528 A1 | 8/2010 | McCauley | |
| 2013/0162365 A1* | 6/2013 | Otaguro | G01P 21/00 333/17.1 |
| 2014/0063652 A1* | 3/2014 | Otani | G11B 33/08 360/97.19 |

* cited by examiner

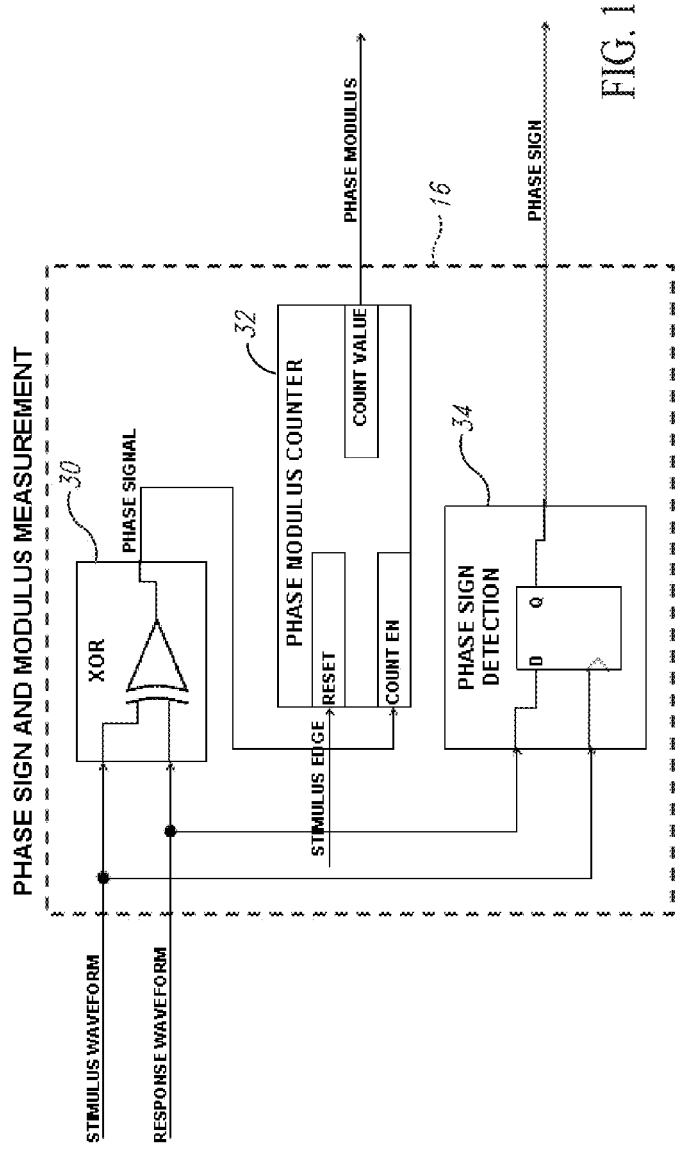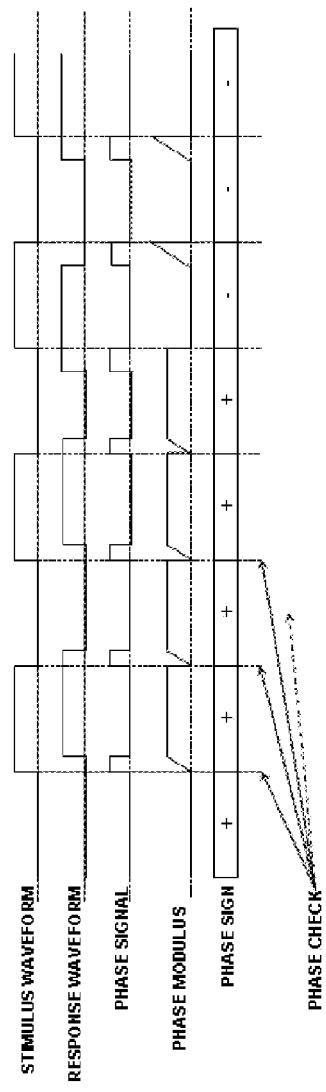
FIG. 12A
FIG. 12B

METHOD AND CIRCUIT FOR DETERMINING RESONANT FREQUENCIES OF A RESONANT DEVICE

BACKGROUND

Technical Field

This disclosure relates to resonance frequency detectors and more particularly to a method and a circuit for determining resonance frequencies of a resonant device, and a method of filtering an output of a resonant device.

Description of the Related Art

Hard disk drive (HDD) applications use shock sensors (SS) in order to avoid unwanted write-read errors due to voice coil motor (VCM) harm caused by disk displacements that are due external causes (i.e. bumps, kicks, motor driving, mechanical stresses).

Unfortunately, these sensors have a mechanical resonance frequency that is close to their signal bandwidth and with amplitude that is several decibels above sensor sensitivity. Therefore, noise at this resonance frequency may be amplified and may even dangerously saturate amplification channels causing distortion of useful signals and long recovery times.

Different approaches are known in literature to prevent saturation caused by unwanted resonance peaking. They consist substantially in either:

- low pass filtering the signals provided by the shock sensor before providing them to the respective amplification stages;
- notch filtering the sensor signals to selectively attenuate certain frequency components.

The first technique reduces the useful signal bandwidth, and the second technique may be correctly implemented only if the information about the resonance frequency is known.

The electrical equivalent circuit of a piezoelectric shock sensor is substantially a capacitor Cp connected electrically in parallel with a RLC series circuit (Cs-Rp-Ls), as shown in FIG. 1. The equivalent impedance is given by the following formula:

$$Z_{sensor}(j\omega) = \frac{1}{j\omega C_P}\left(\frac{\omega^2 - \omega_P^2}{\omega^2 - \omega_S^2}\right) = \frac{1}{j\omega C_P}\frac{Z(j\omega)}{P(j\omega)}$$

wherein, for sake of clarity, zeros and poles of the impedance $Z_{sensor}$ are the zeroes of the polynomials $Z(j\omega)$ and $P(j\omega)$, respectively.

FIG. 2 shows the shock sensor (Cs, Cp, Rp, Ls) having first and second terminals IN, INP respectively coupled to inverting and non-inverting inputs, respectively, of a low noise amplifier 2 having an output OUT. A first parallel circuit 4 of a resistor $R_F$ and capacitor $C_F$ is coupled between the first terminal IN and the output OUT, and a second parallel circuit 6 of a resistor $R_F$ and capacitor $C_F$ is coupled between the second terminal INP and a reference terminal REF. In HDD applications, signals provided by the shock sensor are amplified by the low noise amplifier 2 in order to get noise immunity against physical noise (i.e., flicker and thermal noise) and noise related to external sources (i.e. coupled switching noise, RF interferences). For this reason, the zeroes of the polynomial $Z(j\omega)$ cause resonance peaks in the AC response of the amplification stage:

$$V_{OUT} = \frac{2C_P}{C_F}\left(\frac{P(j\omega)}{Z(j\omega)} + 1\right)v_{noise},$$

wherein $v_{noise}$ is a noise voltage in input to the sensor.

For the above reasons, a reliable method of determining a resonance frequency of a device would be desirable.

The published US Patent Application No. 2010/0064809 discloses a system and a method for determining a mechanical resonance frequency of a sensor, consisting in applying a bias pulse signal to the sensor, detecting zero crosses of the voltage response of the sensor and determining the resonance frequency of the sensor in function of the detected zero-crosses.

Unfortunately, this prior method is not very accurate. Indeed, it is relatively difficult to determine with a high precision the instants in which the output voltage of the sensor nullifies, because of external disturbances (i.e., RF interferences, running clocks) and of the limited sensitivity of zero-cross detectors.

BRIEF SUMMARY

A simple and very accurate method of determining a resonance frequency has been devised. The novel method may be applied for determining a resonance frequency of any resonant device, such as a shock sensor or an accelerometer.

According to this disclosure, the resonant device is stimulated with a periodic input signal having a frequency chosen in a pre-established frequency interval, a frequency value for the periodic input signal is determined in the pre-established frequency interval for which the phase-difference between the periodic input signal and a corresponding periodic output signal of the resonant device is minimum, and a flag adapted to indicate that a resonance frequency has been determined and signals representing the value of the frequency of the periodic input signal are generated.

According to an embodiment of the novel method, the phase-difference between the periodic input signal and the corresponding periodic output signal is compared with a threshold. Depending on whether the threshold is crossed or not, a flag that a resonance frequency has been determined and signals representing the value of the frequency of the periodic input signal are generated, otherwise the method restarts using a periodic input signal having a different frequency chosen in the pre-established frequency interval.

According to yet another embodiment, the periodic input signal is a square-wave.

A particularly simple and accurate circuit for determining the resonance frequency of a resonant device, comprises:

a square-wave generator configured to stimulate the resonant device with a square-wave input signal;

an XOR gate configured to be input with the square-wave input signal and with the corresponding periodic output signal of the resonant device;

a processor configured to receive a logic XOR signal output by the XOR gate, and adapted to determine the duty-cycle of said logic XOR signal, to determine the phase-difference upon the duty-cycle and to control the square-wave generator for adjusting the frequency of the square-wave input signal.

A method of filtering an output of a resonant device is also disclosed.

BRIEF DESCRIPTION OF THE SEVERAL VIEWS OF THE DRAWINGS

FIG. 12A is a block diagram of a circuit for generating signals representing the phase difference between two square-wave signals.

FIG. 12B shows waveforms of the signals produced in the circuit of FIG. 12A.

DETAILED DESCRIPTION

Figure 2:
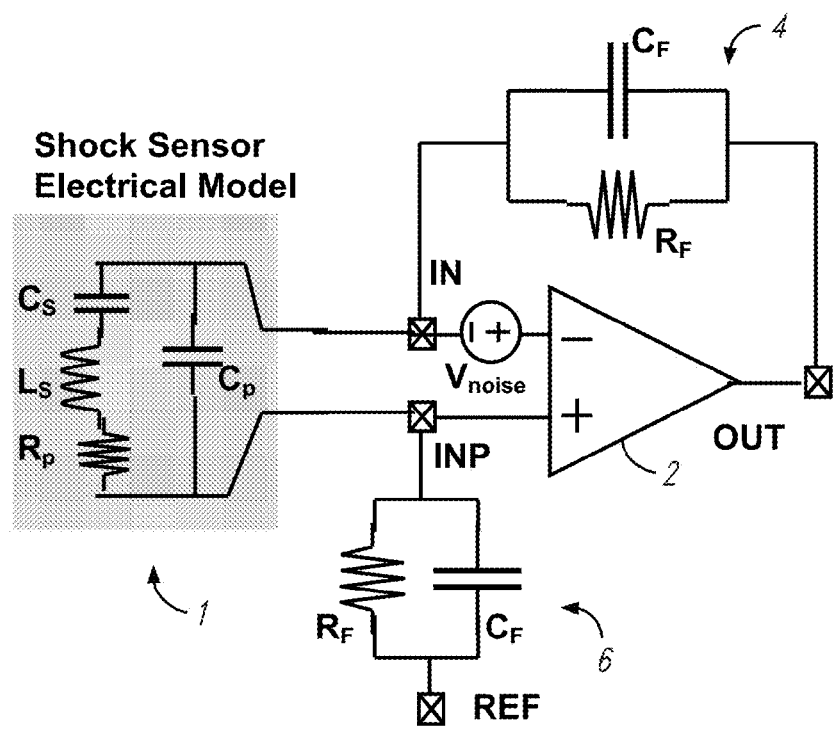
FIG. 2 shows a known amplification stage for a piezo-electric shock sensor.

In the ensuing description reference will be made to the particular case in which the resonant device, the resonance frequency of which is to be determined, is a shock sensor coupled to a respective amplification stage as shown in FIG. 2, though the disclosed methods and circuits may be validly applied, mutatis mutandis, for determining the resonance frequency of any device.

The proposed method can be used to get information about resonance frequency for shock sensors used in hard disk drive (HDD) applications. In general, it may be used to detect a resonance frequency of a piezoelectric motion detection sensor and it can be used in conjunction with a tunable notch filter inserted at an intermediate gain stage in order to realize a system with large bandwidth and gain substantially without risks of saturating because of input noise at the resonance frequency.

Figure 3:
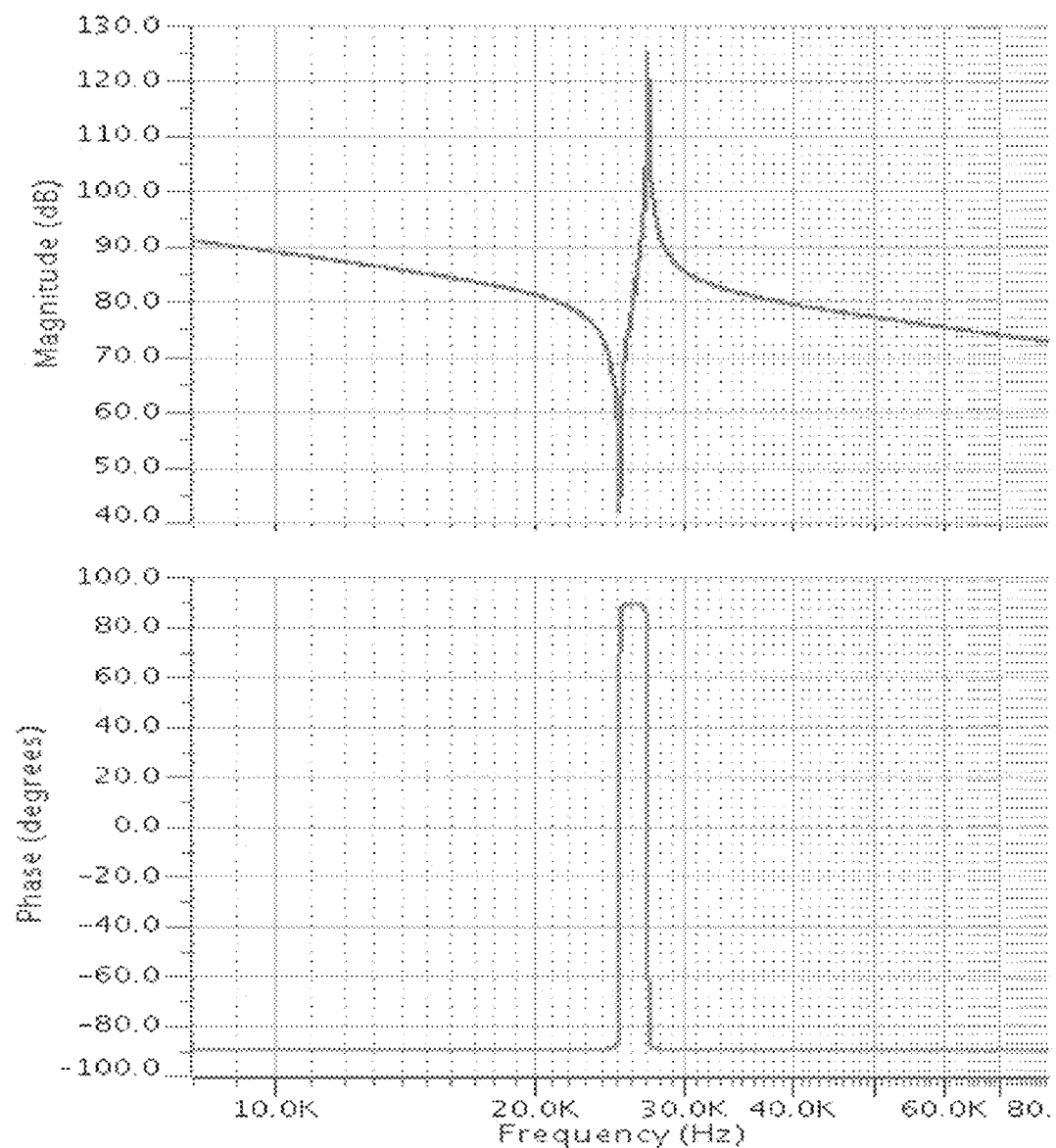
FIG. 3 shows exemplary phase and amplitude spectra of a shock sensor.
Figure 4:
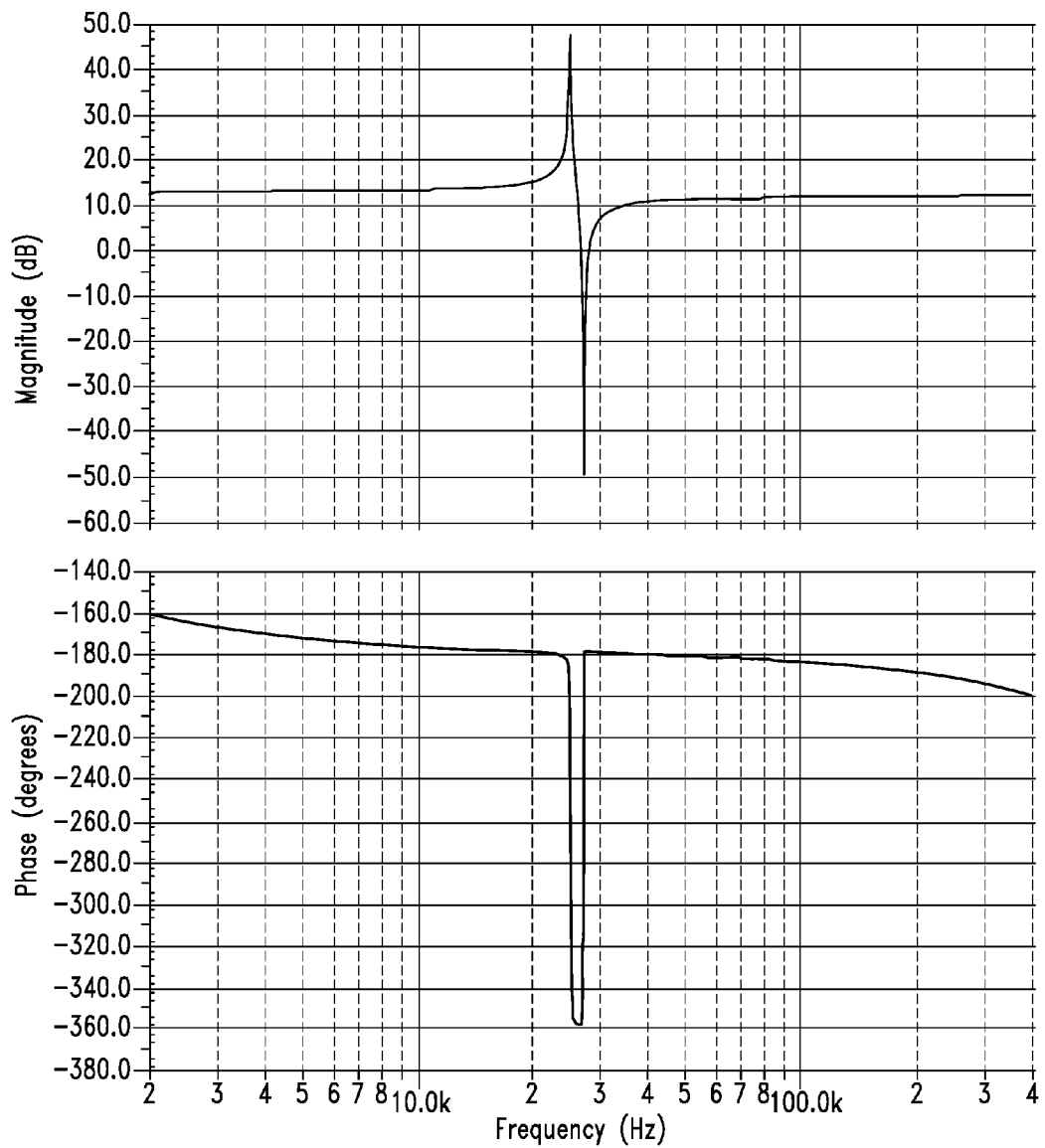
FIG. 4 shows exemplary spectra of the AC response of an amplification stage for piezoelectric shock sensor.

Exemplary amplitude and phase spectra of the known circuit of FIG. 2 are depicted in FIG. 4. The spectra of the AC response of the sensor are shown in FIG. 3. FIGS. 3 and 4 show that the phase spectra of the sensor have a positive or a negative peak substantially centered about the resonance frequency. According to this disclosure, this property is exploited to determine the resonant frequency of a sensor.

A method according to one embodiment of the present disclosure is substantially based on a phase lag measurement using periodic signals, such as for example sinusoidal signals or square wave signals, and allows to determine a resonance frequency with an enhanced noise immunity with respect to prior methods.

According to the proposed method, a resonant device (e.g., a shock sensor) is stimulated with a periodic signal. If the frequency is lower than resonance frequency, the electrical response of the shock sensor is similar to that of a capacitor (i.e., 90° delay with respect to the driving signal). By varying the frequency of the stimulation signal from low frequencies up to frequencies close to the resonance frequency of the shock sensor, the phase lag between the input and output signals of the shock sensor decreases till reaching a minimum value in proximity of the resonance frequency. By increasing further the frequency of the stimulation signal, the phase lag increases again and tends toward 90° at frequencies far from the resonance frequency. According to this disclosure, the resonance frequency is determined by determining the frequency at which this minimum is attained, which in one embodiment is determined to be a frequency at which this phase lag is smaller than a certain threshold.

Figure 5A:
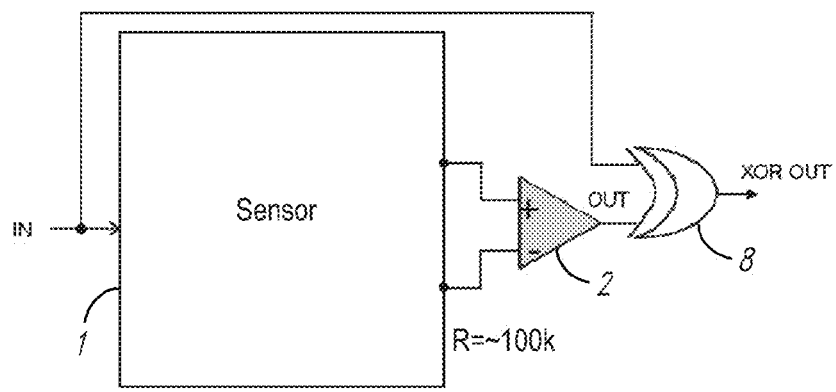
FIG. 5A shows a novel basic circuit for stimulating a shock sensor.
Figure 5B:
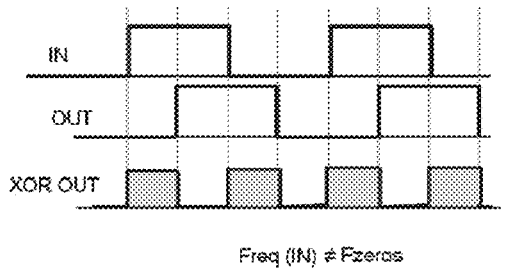
FIGS. 5B and 5C show exemplary time graphs of the input and output signals thereof.
Figure 5C:
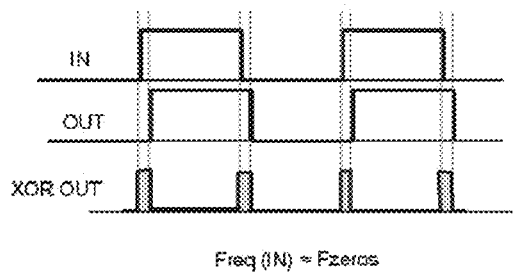

A circuit for implementing the novel method is shown in FIG. 5A. The sensor 1 is stimulated with a periodic square-wave stimulation signal IN which causes the low noise amplifier 2 to generate a corresponding square-wave output signal at the output OUT. A logic XOR gate 8, input with the stimulation signal IN and the output signal at OUT, generates a XOR signal (XOR OUT) the duty cycle of which represents the phase lag between the signals IN and OUT. As shown in FIGS. 5B and 5C, by varying the frequency of the periodic signal IN, it is possible to notice that the duty-cycle of the XOR signal is minimum substantially in correspondence of the resonance frequency.

Figure 6:
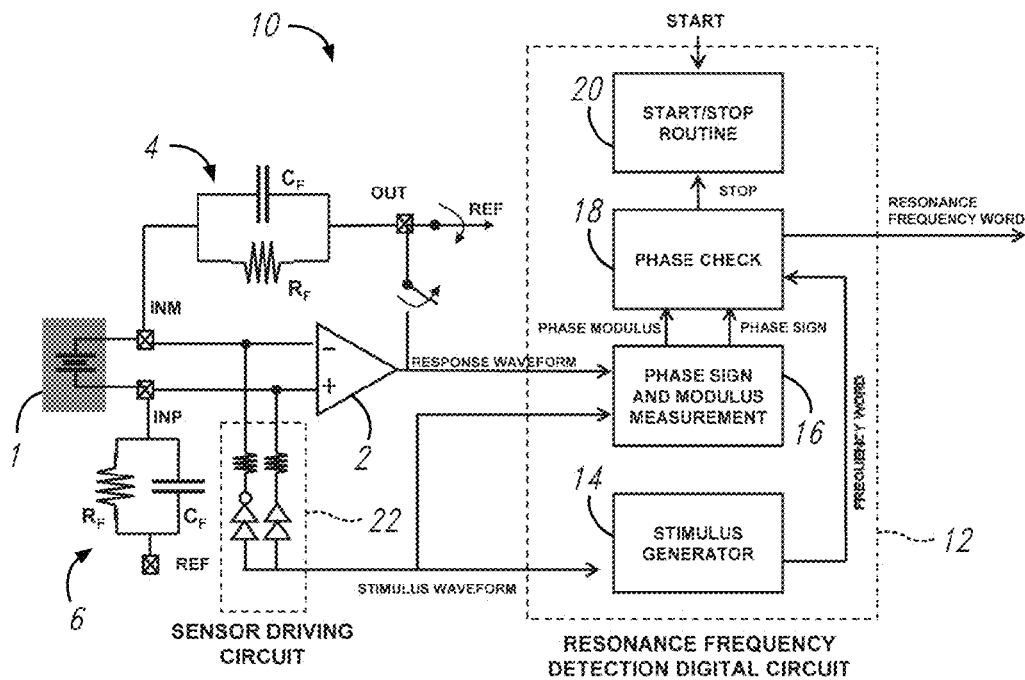
FIG. 6 depicts another novel circuit for determining the resonance frequency of a shock sensor.

Another detection circuit 10 that could be used to detect a resonance frequency of a device, such as the shock sensor 1, is shown in FIG. 6. The circuit 10 includes a digital circuit 12 that outputs a resonance frequency based on a response signal (RESPONSE WAVEFORM) produced by the low noise amplifier 2. The digital circuit 12 includes a stimulus generator 14, a phase measurement block 16, a phase check block 18, and a start/stop module 20. The detection circuit 10 also includes an analog driving circuit 22 coupled between the stimulus generator 14 and the terminals of the shock sensor 1.

The stimulus generator 14 provides a stimulus signal (STIMULUS WAVEFORM) to the driving circuit 22 and the phase measurement block 16, and provides to the phase check block 18 a digital word (FREQUENCY WORD) representing the frequency of the stimulation signal. The phase measurement block 16 measures the phase modulus and sign of a phase difference between the stimulus signal and the response signal. In particular, phase measurement block 16 outputs to the phase check block 18 a phase modulus signal (PHASE MODULUS) representing the absolute value of the phase lag between the response signal and the stimulation signal, and a phase sign signal (PHASE SIGN) representing the sign of the phase lag between the response signal and the stimulation signal. The phase check block 18 uses the values coming from the stimulus generator 14 and the phase measurement block 16 to detect the resonance frequency. The start/stop module 20 handles start and stop routine conditions.

The driving circuit 22 stimulates the sensor 1 with a periodic signal, for example a square wave signal, based on the stimulus signal received from the stimulus generator 14. The comparator (low noise amplifier 2) provides a square wave having a phase equal to the phase of the signal input to the sensor, and the digital circuit 12 evaluates the phase lag between the input stimulus and the sensor output signal. The input stimulation signal frequency is varied in a frequency range. Once the output signal of the sensor reaches a target phase lag with respect to the input driving signal (for example 60°, or 45°), the input signal stimulation frequency corresponding to the target phase lag is assumed to be equal to the sensor amplifier peaking frequency.

The sensor driving circuit 22 is connected to the sensor terminals and to the sensor amplifier terminals (INM and INP) and it injects into the sensor the stimulation signal STIMULUS WAVEFORM. A possible implementation of this circuit may be as shown in FIG. 6, with a cascade of digital gates whose last stage can be tri-stated, and two resistors connected between the driving gates and the sensor terminals INP and INM. These two resistors limit the energy transferred to the sensor avoiding rail-to-rail voltage swings on INM and INP and allow the transfer of energy toward the sensor. A detailed view of the sensor driving circuit of FIG. 6 is shown in FIG. 7.

Figure 7:
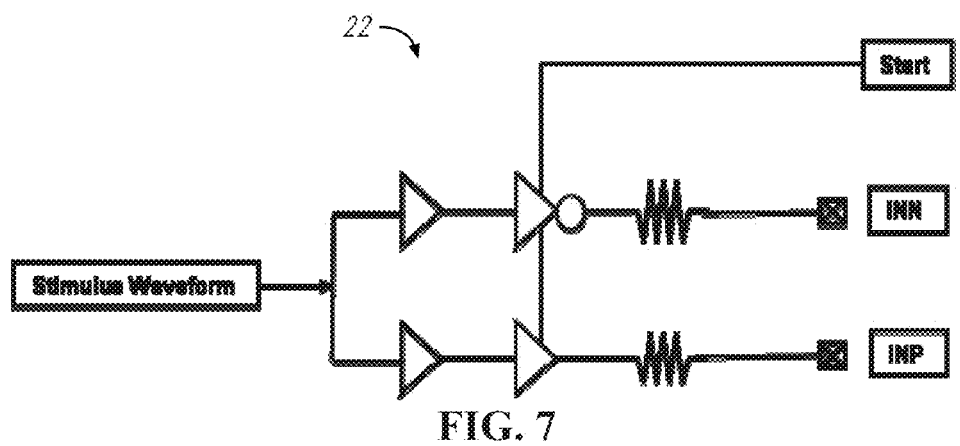
FIG. 7 shows a circuit for driving a shock sensor with a square wave.

A similar function to that one implemented by the circuit shown in FIG. 7 could be obtained using a digital controlled current mirror adapted to sink and to deliver a current depending on the digital value of the input stimulation signal STIMULUS WAVEFORM. A comparator providing a signal with the same phase of the signal provided to the shock sensor is used in the detection circuit in order to monitor the phase lag between stimulation and sensor signals.

To perform this function, it is possible to use either a dedicated comparator or the sensor amplifier itself in open loop configuration. In the latter case, a switch between the OUT pin and the output of the sensor amplifier is opened, the OUT terminal being connected to an internal reference buffer driving pin REF. With the proposed switches connection, the external components constitute a balanced network that, approximately, does not affect sensor singularities. Therefore, the transient behavior of the signals INM and INP will be related to shock sensor singularities.

According to common techniques, it is possible to arrange sensor driving circuit and the comparator circuit in order to get a single ended driving and reading system, that may be useful when the INP terminal is connected directly to the REF terminal.

Figure 8:
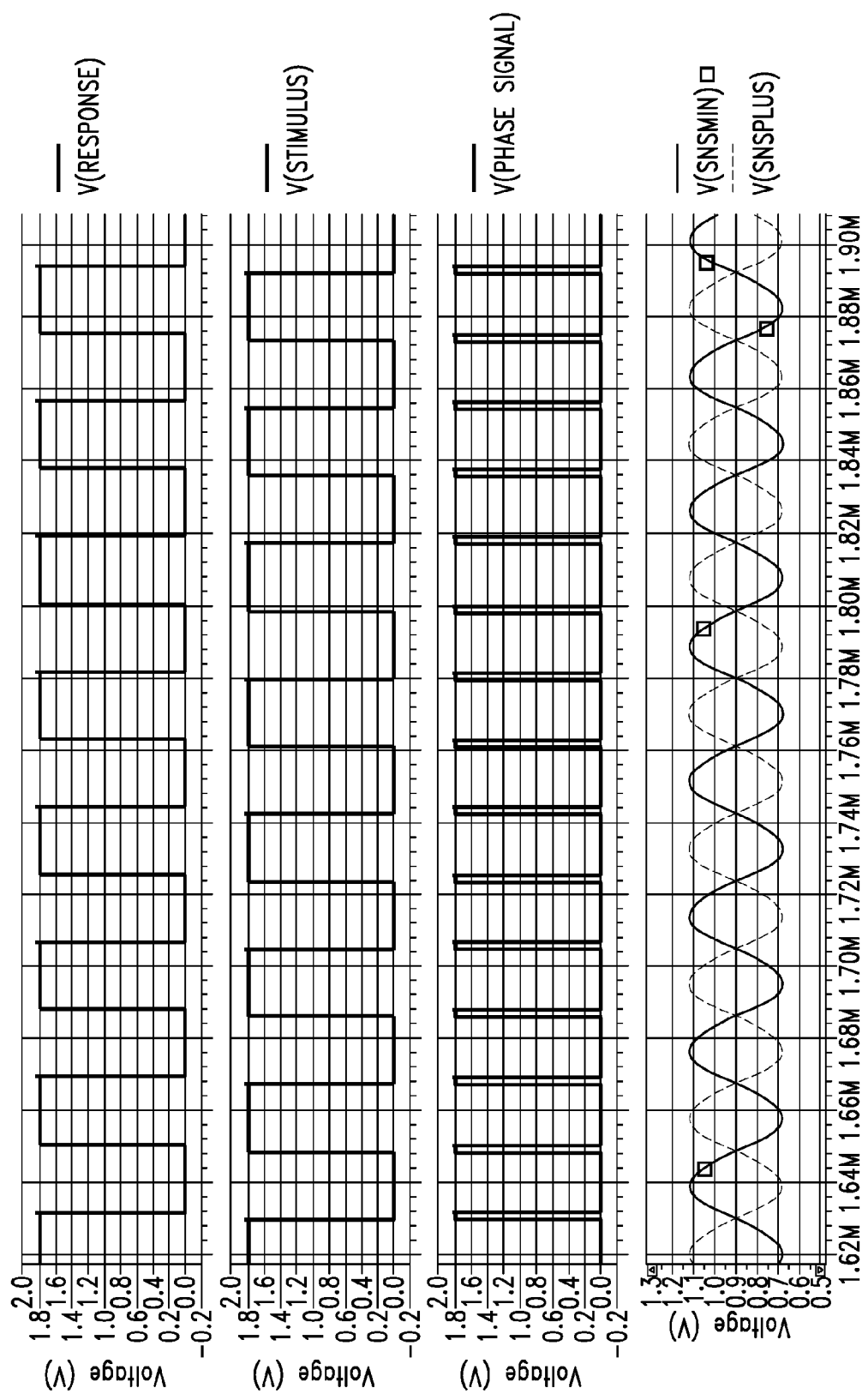
FIG. 8 shows exemplary graphs of the shock sensor output voltage and of the stimulation voltage at a frequency relatively close to the resonance frequency of the sensor.
Figure 9:
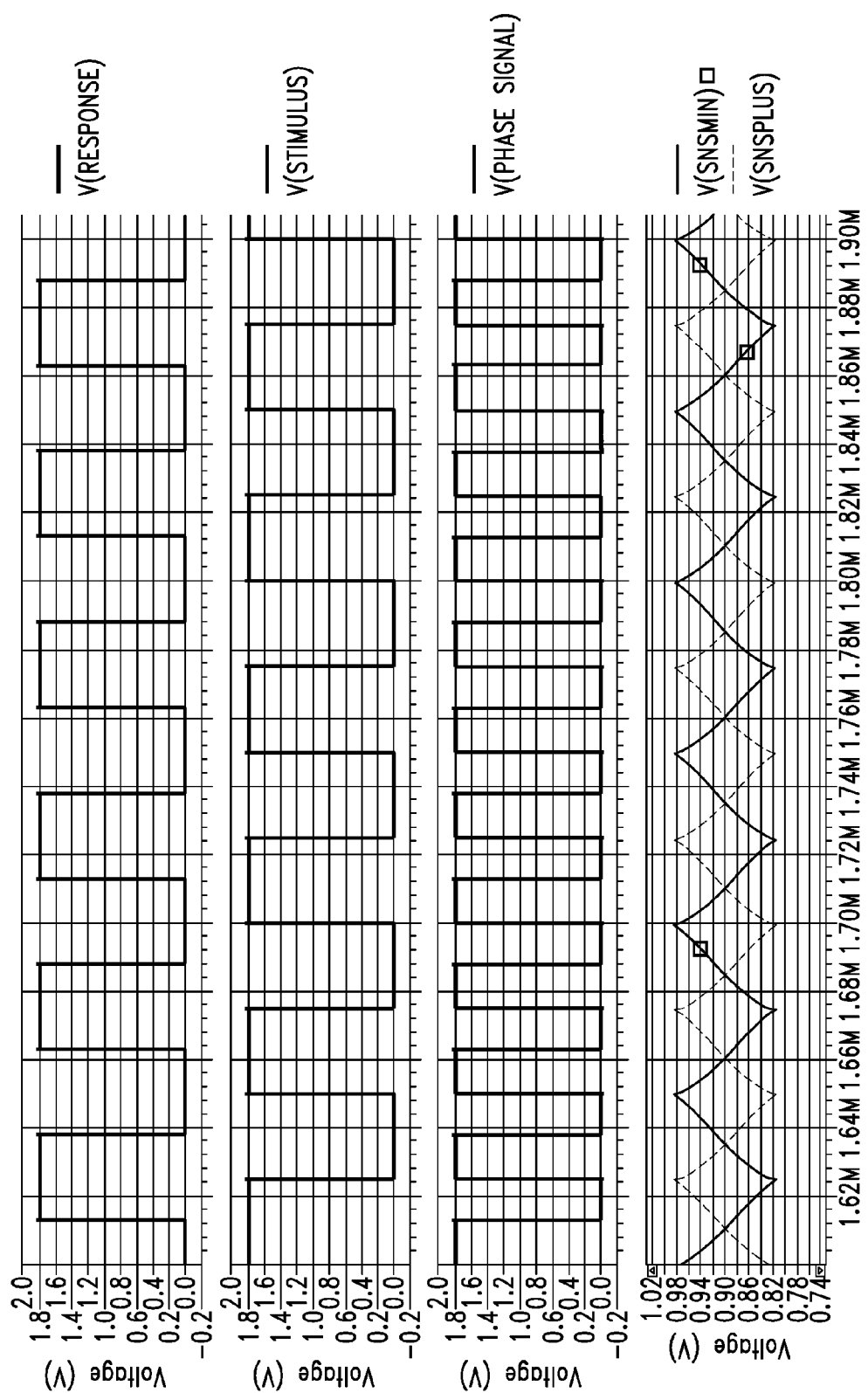
FIG. 9 shows exemplary graphs of the shock sensor output voltage and of the stimulation voltage at a frequency relatively far from the resonance frequency of the sensor.

A snapshot of signal applied to the sensor and phase information is shown in FIGS. 8 and 9. In FIG. 8 the input frequency is close to the sensor singularities frequency, in FIG. 9 the frequency of the driving signal is far from sensor resonance frequency.

Figure 1:
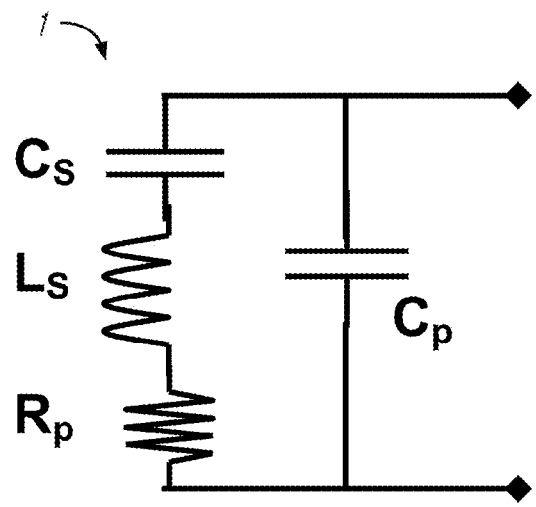
FIG. 1 is an electrical equivalent circuit of a shock sensor.

When the driving signal frequency is close to sensor poles and zeros, the energy transferred from driving circuit to sensor itself causes large oscillation at sensor terminals and, after a phase settling transient, the phase difference between driving signal and sensor signal (STIMULUS WAVEFORM vs RESPONSE WAVEFORM) tends to decrease from 90° toward 0° depending on sensor loss resistor (i.e. Rp in RLC series equivalent, refer to FIG. 1). When the driving signal has a frequency that is relatively far from sensor singularities, the shock sensor shows a behavior similar to that of a capacitor. This case is shown in FIG. 9, wherein the driving signal and the sensor signal are orthogonal to each other (90° phase lag). Information about phase difference between sensor phase signal and driving signal are used by the circuit for determining the resonance frequency.

Figure 10:
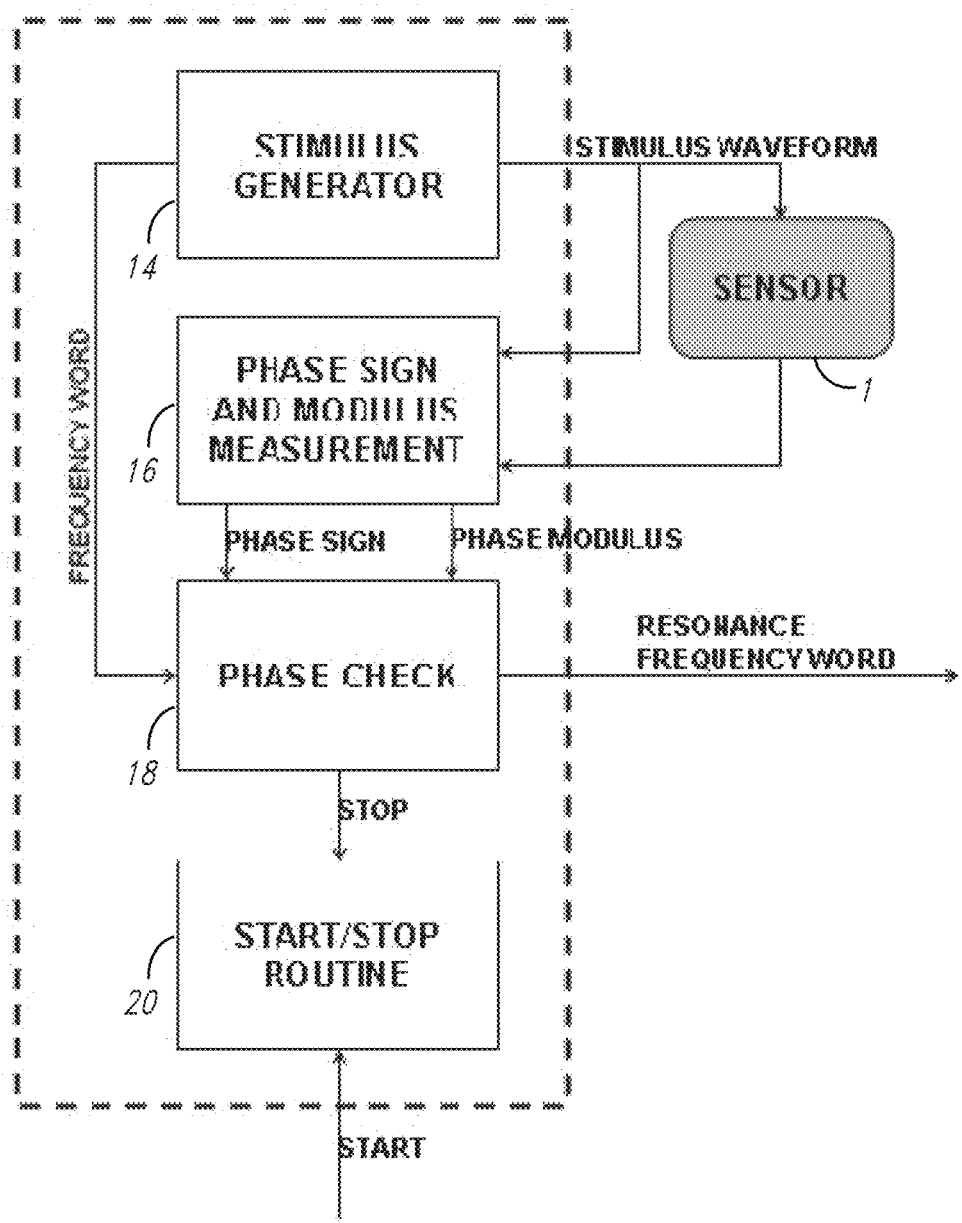
FIG. 10 is a block diagram of a detector of the resonance frequency of a shock sensor.

According to the embodiment shown in FIG. 10, the novel circuit is composed of the stimulus generator 14, phase measurement block 16, phase check block 18, and control block 20. The stimulus generator 14 provides a stimulus waveform to excite the sensor through an analog driver circuit (not shown in figure). The phase measurement block 16 provides a digital information about the phase relationship between stimulus and sensor output waveforms. The phase check block 18 uses the values coming from the stimulus generator block and from the phase measurement block to determine the resonance frequency. The control block 20 mainly handles the start and stop of the algorithm. The output of the routine is a digital word representing the sensor resonance frequency.

The purpose of the stimulus generator block 14 is to create a stimulus waveform having a frequency ranging from a start frequency to a stop frequency. The stimulus waveform is generated with a frequency value maintained for a programmable time interval. This time interval will be sufficient to allow the sensor to settle. The frequency variation can be performed in both directions (from minimum to maximum frequency or from maximum to minimum frequency). The frequency step resolution will be fixed depending on the sensor characteristics.

Figure 11A:
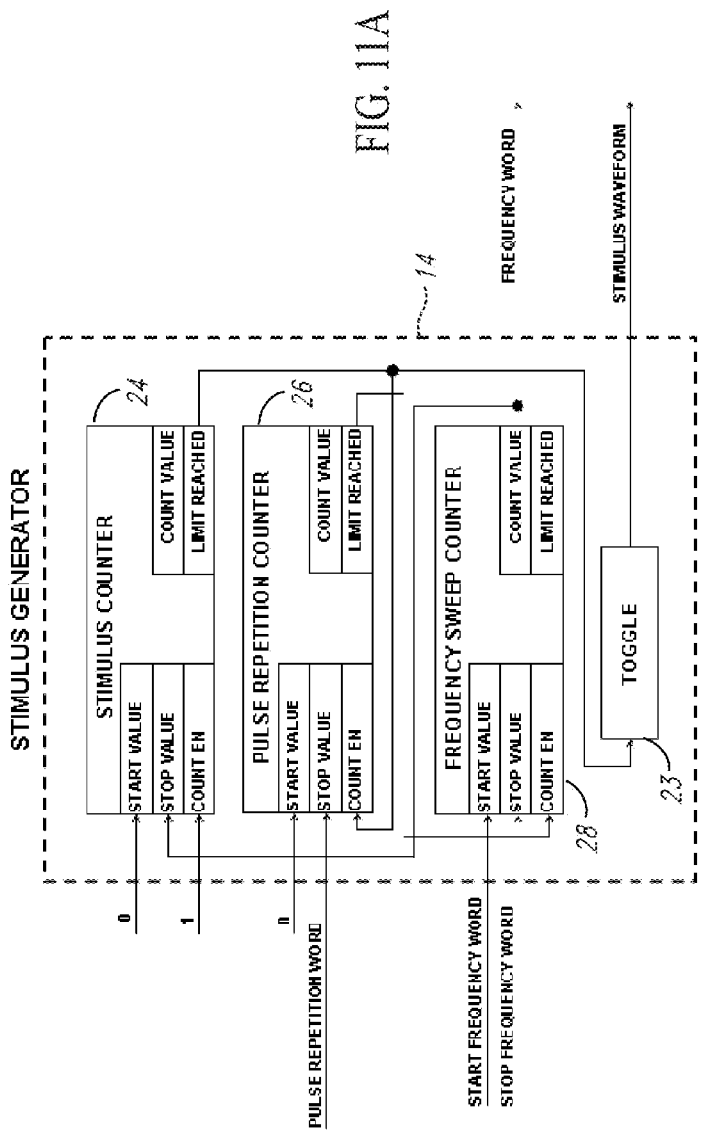
FIG. 11A is a block diagram of a circuit for generating a square-wave stimulus for a shock sensor.

As shown in FIG. 11A, one embodiment of the stimulus generator block 14 includes a toggle block 23 and three counters: a stimulus counter 24, a pulse repetition counter 26, and a frequency sweep counter 28. The meaning of each block and of each signal of which is summarized in the following table:

| | |
|---|---|
| STIMULUS COUNTER | increments its value until the frequency sweep counter value is reached, then the value is reset and starts again |
| START VALUE | Start value for the counter |
| COUNT EN | Enable for the counter |
| COUNT VALUE | Counter value |
| LIMIT REACHED | Indicates when the COUNT VALUE reaches the STOP VALUE |
| PULSE REPETITION COUNTER | Counter to control the frequency step duration. It counts the half-periods of the STIMULUS WAVEFORM at the same frequency. The number of half-periods is equal to PULSE REPETITION WORD |
| PULSE REPETITION WORD | Parameter indicating the number of half-periods of the STIMULUS WAVEFORM at the same frequency |
| FREQUENCY SWEEP COUNTER | Counter indicating the period of the output waveform at each step. It counts between START FREQUENCY and STOP FREQUENCY WORD |
| WORD | |
| START FREQUENCY WORD | Start value for FREQUENCY SWEEP COUNTER |
| STOP FREQUENCY WORD | stop value for FREQUENCY SWEEP COUNTER |
| FREQUENCY WORD TOGGLE | FREQUENCY SWEEP COUNTER value Toggles its output when the input goes from low to high |
| STIMULUS WAVEFORM | Stimulation signal |

Figure 11B:
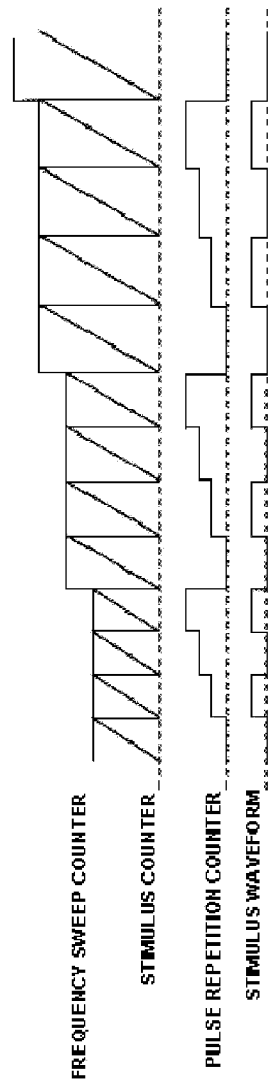
FIG. 11B shows waveforms of the signals produced in the circuit of FIG. 11A.

The frequency sweep counter 28 indicates the period of the output waveform at each step, the pulse repetition counter 26 controls the step duration and the stimulus counter 24 increments its value until the frequency sweep counter value is reached, as depicted in the waveforms shown in FIG. 11B. When this event occurs, the stimulus counter 24 is reset and the stimulus waveform is toggled by the toggle block 23. The effect is that the frequency of the stimulus waveform depends on the frequency sweep counter value and on the frequency of the clock that feeds the stimulus counter 24.

FIG. 12A shows a possible implementation of phase sign and modulus measurement block 16, includes an XOR gate 30, a phase modulus counter 32 and a phase sign detection block 34, which is implemented using a D flip-flop. The XOR gate 30 has first and second inputs configured to receive the stimulus signal and the response signal, respectively, and an output configured to provide a phase signal. The phase modulus counter 32 is configured to be reset by a leading or trailing edge of the stimulus signal and includes a count enable input coupled to the output of the XOR gate, a reset input configured to receive the stimulus signal, and an output configure to provide a count value equal to the phase modulus provided to the phase check block 18. The phase sign detection block 34 has first and second inputs configured to receive the stimulus signal and the response signal, respectively, and an output configured to provide the phase sign to the phase check block 18. In this implementation, the modulus is evaluated using the XOR gate 30 and the phase modulus counter 32 and the sign is directly detected by the phase sign detection block 34 using the edge relationship between the input waveforms. FIG. 12B shows the waveforms for the various signals according to one embodiment.

Figure 13:
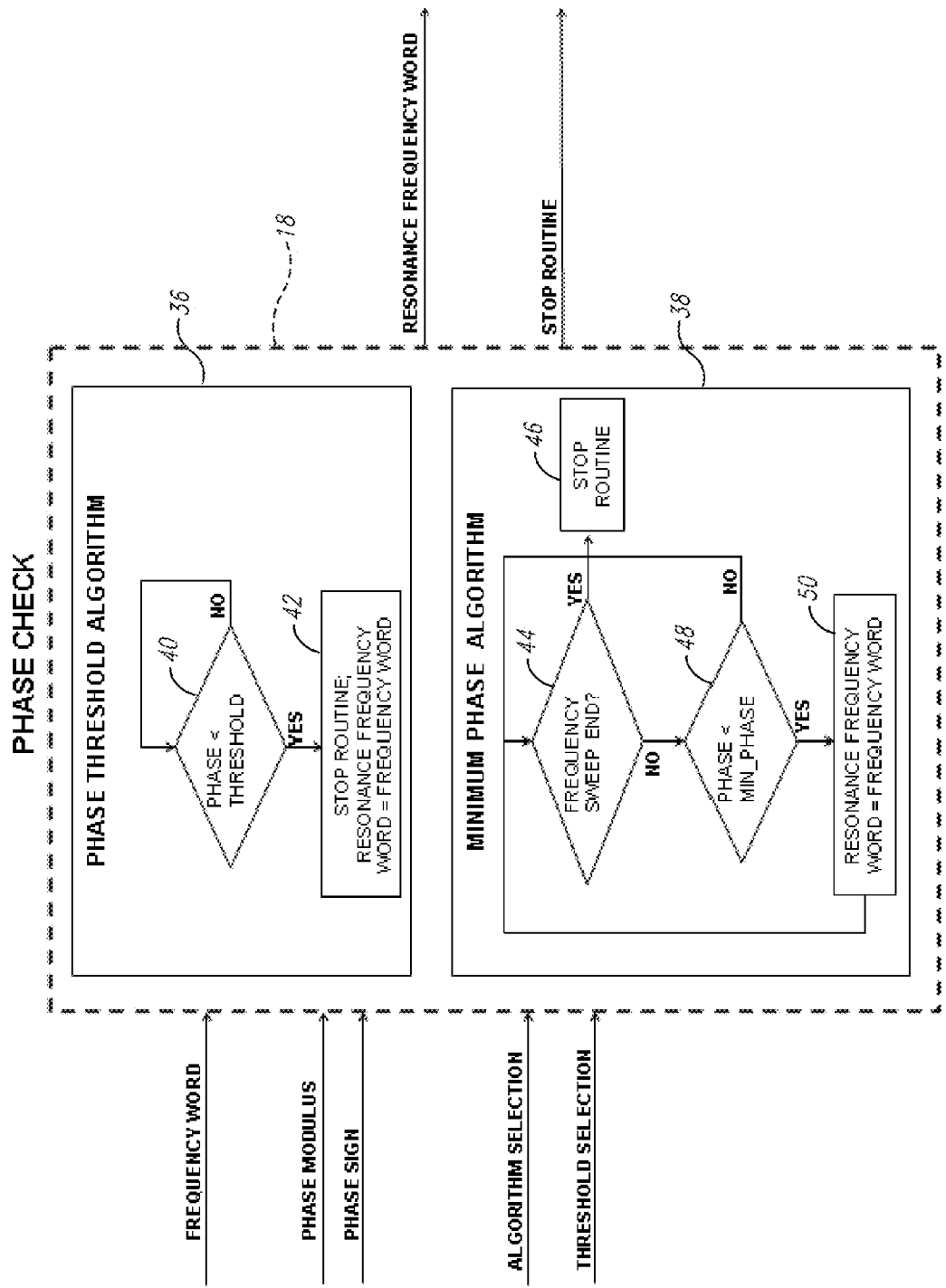
FIG. 13 is a flow chart of the algorithm used for generating a digital word representing the detected resonance frequency.

FIG. 13 shows the phase check block 13 with decision algorithms used to detect the resonance frequency. It is possible to choose either a phase threshold algorithm 36 or a minimum phase algorithm 38. In step 40, the phase threshold algorithm 36 compares an incoming phase (phase module and phase sign), received from the phase measurement block 16, with a phase threshold that may be hardwired or set dynamically, such as by software instruction. If the incoming phase is not less than the phase threshold, then the phase threshold algorithm 36 returns to step 40 to compare the next incoming phase with the threshold. If the incoming phase is less than the phase threshold, then the phase threshold algorithm 36 outputs the current frequency word, received from the stimulus block 14, as the detected resonance frequency word (step 42).

The meaning of the signals of FIGS. 12A and 13 is summarized in the following table:

| | |
| --- | --- |
| STIMULUS EDGE | Leading or trailing edge event of STIMULUS WAVEFORM |
| PHASE SIGN DETECTION | Flip-Flop or equivalent circuit to detects the sign of the phase between two signals |
| ALGORITHM SELECTION | Parameter to select which type of algorithm is used during the routine |
| THRESHOLD SELECTION | Parameter to select the phase threshold to be used by the PHASE THRESHOLD ALGORITHM |
| STOP ROUTINE | Signal used to stop the routine |

The phase threshold algorithm compares the measured phase with the selected threshold. When the phase is less than the threshold the routine is stopped and the resonance frequency word is determined by the current frequency word.

In the minimum phase algorithm 38, a frequency range is swept and the algorithm stores the frequency word corresponding to the minimum phase evaluated. At the end of the sweep the resonance frequency word represents the stored frequency. In particular, step 44 determines whether the sweeping has reached the end of the frequency range. When the end of the frequency range is reached, the algorithm stops in step 46. The algorithm 38 then checks in step 48 whether the phase received from the phase measurement block 16 is less than a minimum phase threshold. If not, then the algorithm returns to step 44. If the phase received from the phase measurement block 16 is less than the minimum phase threshold, then, in step 50, the algorithm stores the frequency word corresponding to the phase received from the phase measurement block 16 and returns to step 44.

A target lag phase is used by resonance detection circuit 10 in order to stop the frequency sweeping when a certain target phase lag threshold is reached. Once this condition is met, the detection circuit provides a digital representation of sensor zeros frequency that can be used in conjunction with a proper clock generator and a switched capacitor notch filter in order to attenuate resonance tones that may be injected into the amplification channel.

Figure 14:
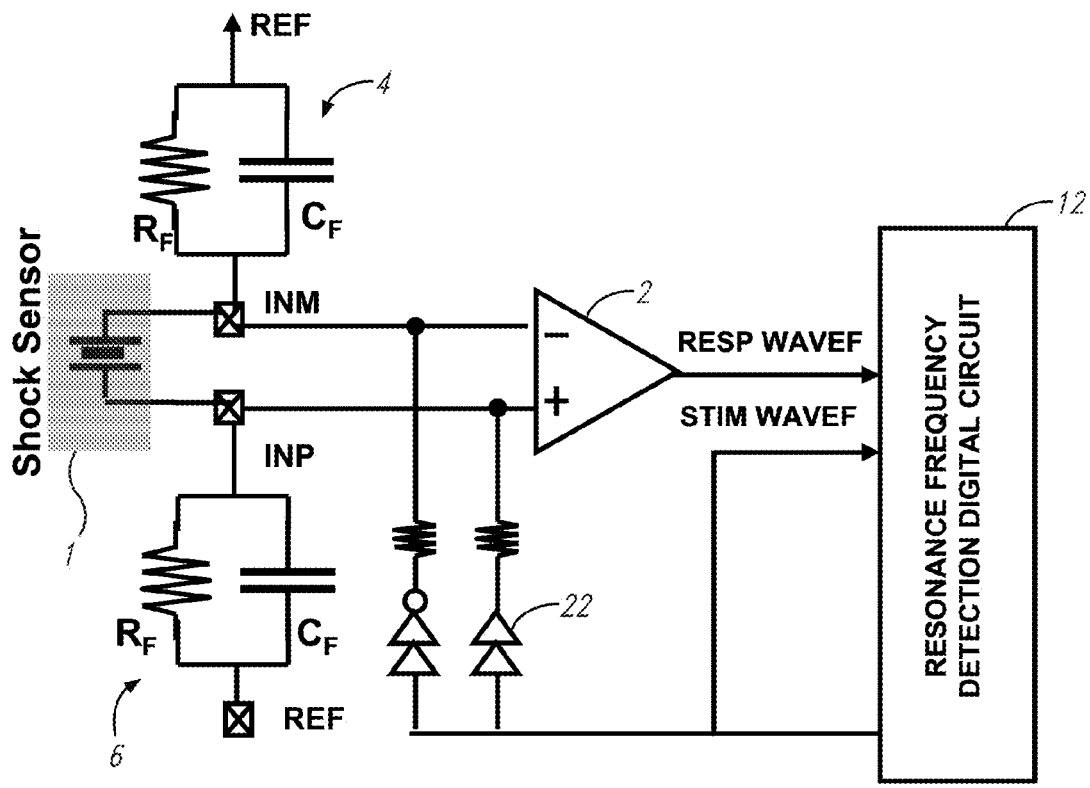
FIG. 14 is a basic scheme of the novel driver of a shock sensor for determining the resonance frequency thereof.
Figure 15:
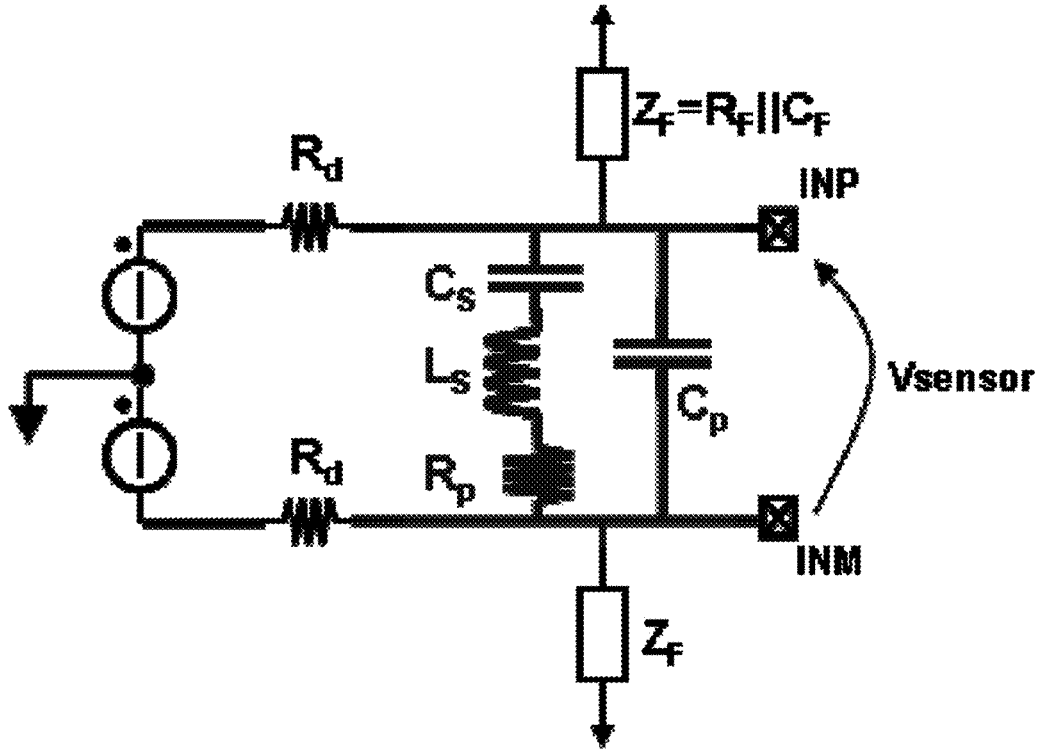
FIG. 15 shows the equivalent circuit of the driver depicted in FIG. 14.

FIGS. 14 and 15 show the phase measurement circuit and its linear equivalent circuit, that may be used to evaluate the AC response of the sensor to external driving excitations in function of the driver impedance $R_d$, of the external feedback components $R_F$, $C_F$ and of the electrical equivalent parameters ($C_P$, $C_S$, $L_S$ and $R_P$) of the sensor 1.

Figure 16:
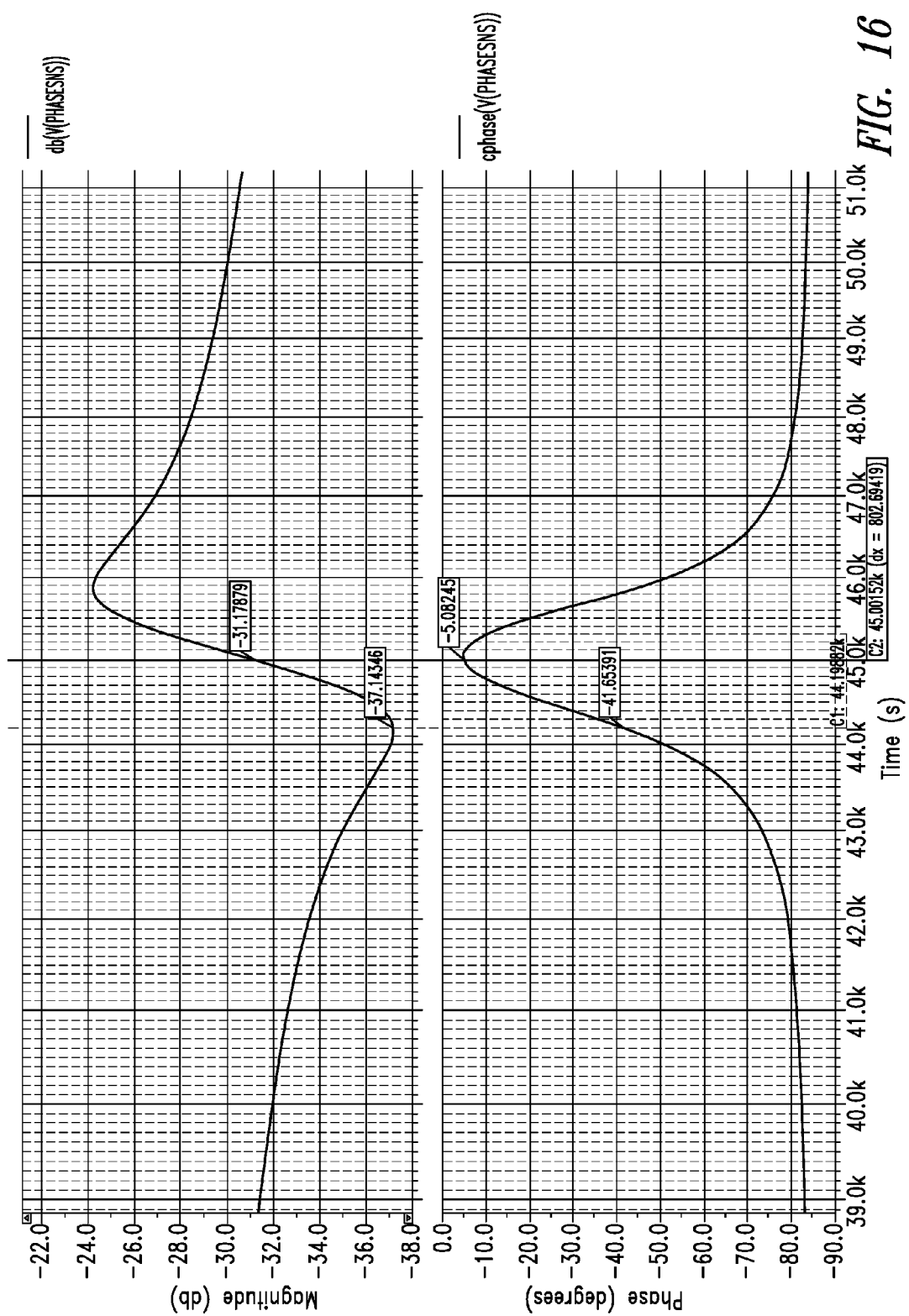
FIG. 16 shows amplitude and phase spectra of the AC response of the sensor driven by the driver of FIG. 14.

FIG. 16 are typical simulation spectra of a sensor of FIG. 15. It is possible to see that the frequency of the zeroes approximately correspond to 45° phase lag in the AC sensor response; it is worth to highlight a minimum phase lag of 45° is also close to the frequency of the zeroes and could be used as a target phase in the resonance search routine.

Using different shock sensors, the phase at zeros frequency changes mainly depending on sensor poles and zeros relationship but also on loss resistance (i.e. the resistance $R_P$ in the equivalent circuit of FIG. 1). The novel technique of sensing the minimum phase lag condition remain the unique method which is able to return sensor amplifier resonance frequency information regardless of the sensor used.

Method Validation

Figure 17:
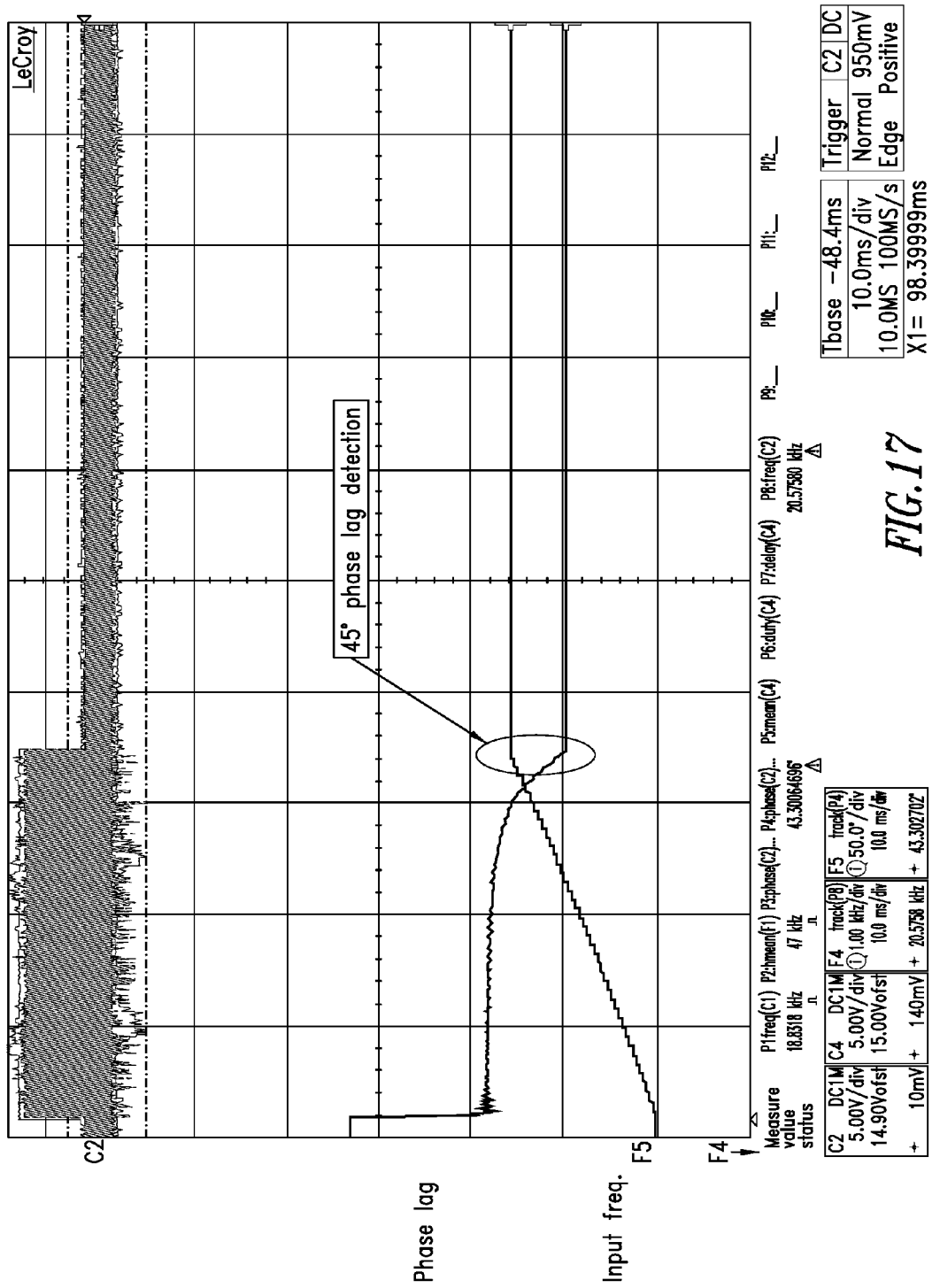
FIG. 17 shows an exemplary simulation graph of the functioning of the novel resonance detector.
Figure 18:
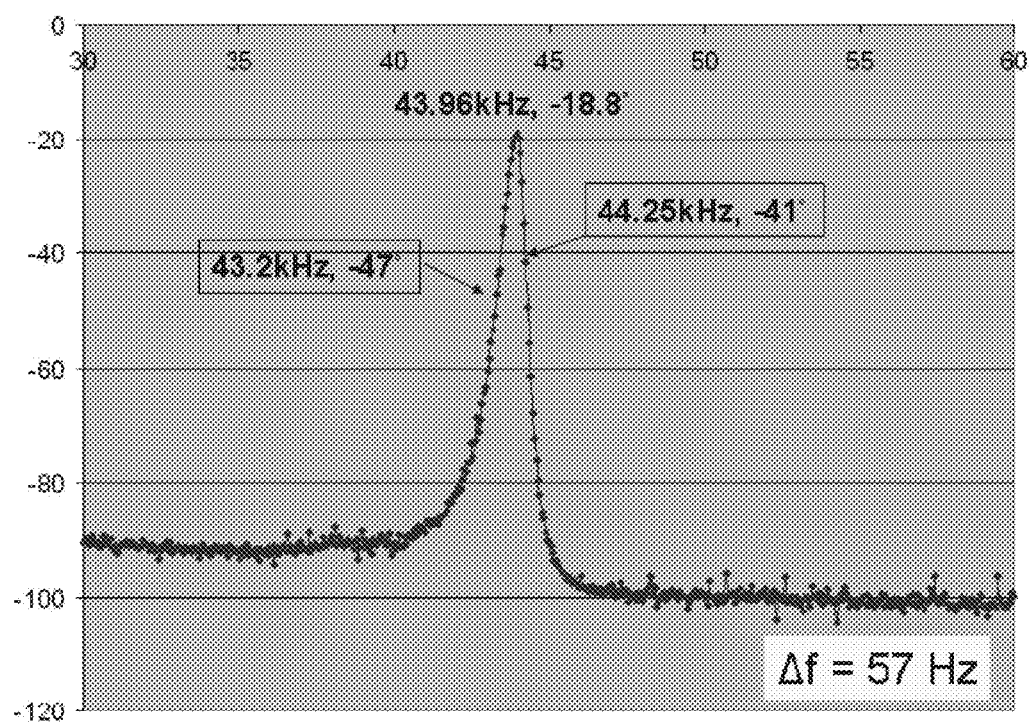
FIG. 18 is an exemplary measurement of phase spectrum of a sensor, obtained using the novel resonance detector.

The proposed method has been tested using an ASIC (Application Specific Integrated Circuit) that implements the proposed algorithm and the desired filtering strategy. FIG. 17 shows an exemplary transient frequency variation of driving signal applied to a common shock sensor and the phase difference between stimulation signal and signal across sensor. In the shown embodiment, the algorithm stops when phase lag crosses a threshold of 45°. In FIG. 18 it is possible to notice that a condition of 45° phase lag corresponds to the resonance frequency of the sensor amplifier stage.

The novel resonance detection circuit may be used alone in order get information about shock sensor resonance frequency but also in conjunction with a filter (such as a notch filter, a switched capacitor filter, etc.) in order to filter out in a refined manner resonance tones that may be present on the sensor amplifier output node (OUT) for avoiding saturation of the signal processing channel.

The novel method for determining a resonant frequency of a resonant device may be used for filtering an output of a resonant device using a generic notch filter.

Figure 19:
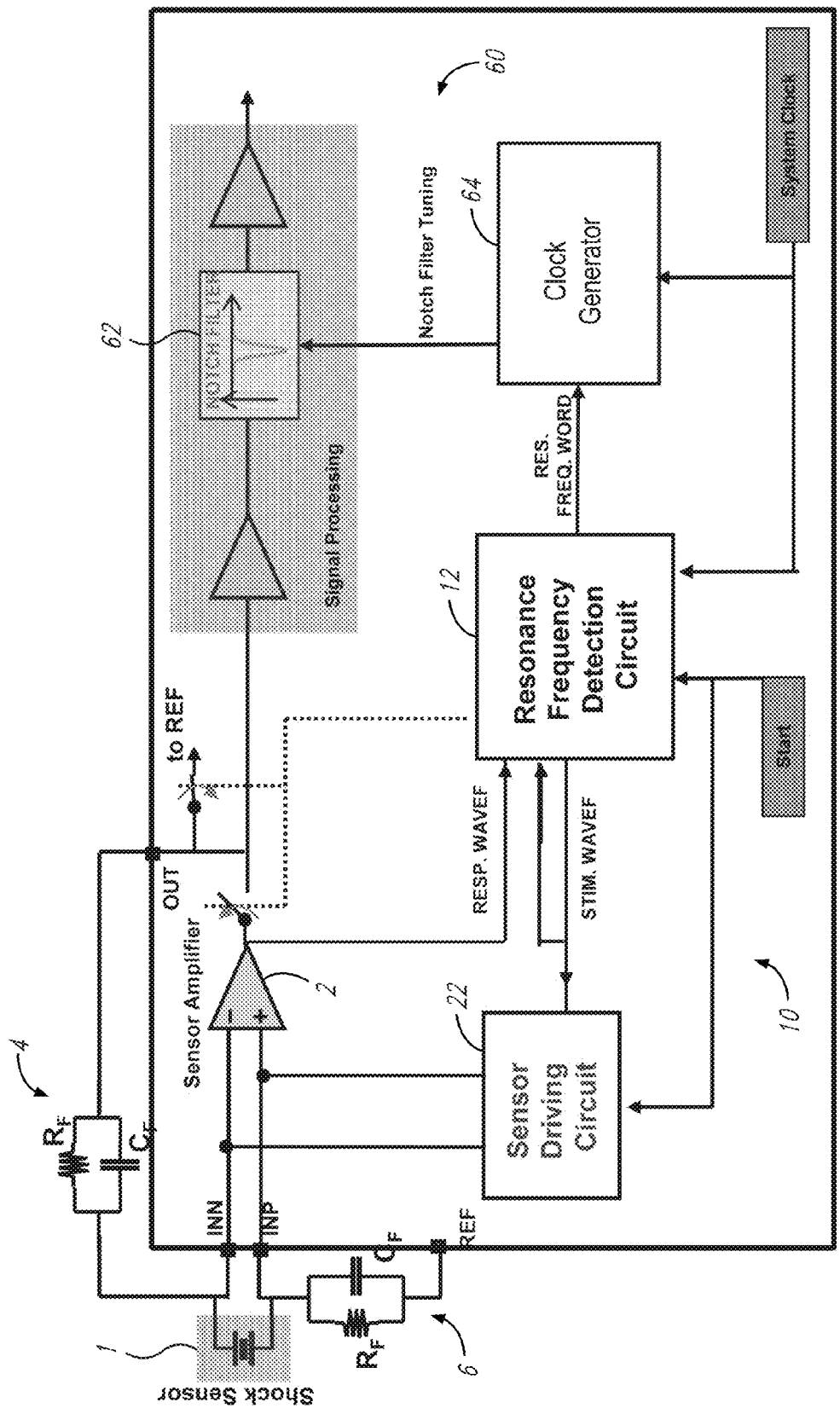
FIG. 19 shows a novel resonance detector connected to a notch filter for filtering out the resonance frequency from the output signal of the sensor.

FIG. 19 shows a system that includes the resonance detection circuit 10 together with a signal processing circuit 60 that includes a notch filter 62 and a clock generator unit 64. The resonance detection circuit 10 configures the sensor amplifier 2 as a comparator in order to get phase information on the signal present on the shock sensor 1 and then starts the detection algorithm, using an input stimulation signal frequency ranging in a frequency range preferably related to the shock sensor singularities frequency. Once the target phase lag condition is met, the digital word representing the sensor amplifier resonance frequency (RES. FREQ. WORD) is stored and used by the clock generator unit 64 to provide the clock for the notch filter 62. In this way notch filter notched frequency will correspond to resonance frequency of shock sensor amplifier 2. The digital resonance frequency determination circuit is also able to perform a frequency sweep from high frequencies toward the lower ones, the direction from low to high frequencies or vice versa being irrelevant. The system of FIG. 19 is adapted to implement these functions, and the meaning of the main signals of the system is summarized in the following table:

| | |
|---|---|
| RESP. WAVEF | Sensor response signal |
| STIM.WAVEF | Stimulation signal |
| RES FREQ WORD | digital word representing the frequency of the stimulation signal |
| START | Routine start signal |

With the shown circuit, the notch filter notched frequency will correspond accurately to the resonance frequency of the shock sensor amplifier 2 and thus eventual noise at the resonance frequency of the sensor is filtered out.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of determining a resonance frequency of a shock sensor, comprising:
   providing to the shock sensor a periodic input signal having a frequency in a frequency interval, the shock sensor being configured to detect a shock imparted to the shock sensor;
   calculating a frequency value for said periodic input signal in said frequency interval for which a phase difference between said periodic input signal and a corresponding periodic output signal of the shock sensor is minimum, the corresponding periodic output signal being an electrical response of the shock sensor to the periodic input signal being provided to the shock sensor;
   generating a signal indicating that the resonance frequency has been determined; and
   generating a signal representing said resonance frequency of the shock sensor as the calculated frequency value of said periodic input signal.

2. The method of claim 1, wherein calculating the frequency value includes:
   comparing said phase difference with a threshold; the method further comprising:
   when said threshold is not crossed, choosing a different frequency value for said periodic input signal in said frequency interval before providing to the shock sensor the periodic input signal having the different frequency value.

3. The method of claim 2, wherein said threshold corresponds to the absolute value of said phase difference of about 45° or greater.

4. The method of claim 1, wherein said periodic input signal is a square-wave input signal.

5. The method of claim 4, wherein calculating the frequency value includes:
   comparing said phase difference with a threshold; the method further comprising:
   when said threshold is not crossed, choosing a different frequency value for said periodic input signal in said frequency interval before providing to the shock sensor the periodic input signal having the different frequency value;
   generating a logic XOR signal corresponding to a logic XOR between said square-wave input signal and the corresponding periodic output signal;
   comparing a duty-cycle of said logic XOR signal with a corresponding level; and
   assessing upon said comparing whether said phase difference surpassed said threshold.

6. The method of claim 1, wherein said frequency interval is a signal bandwidth of the shock sensor.

7. A circuit for generating a signal representing a resonance frequency of a shock sensor, comprising:
   a square-wave generator configured to provide to said shock sensor a square-wave input signal having a frequency in a frequency interval;
   a phase detection circuit configured to calculate a phase difference between said periodic input signal and a corresponding periodic output signal of the shock sensor; and
   a phase check circuit configured to calculate a frequency value for said periodic input signal in said frequency interval for which the phase difference between said periodic input signal and the corresponding periodic output signal of the shock sensor is minimum, the corresponding periodic output signal being an electrical response of the shock sensor to the periodic input signal.

8. The circuit of claim 7, wherein the phase detection circuit includes:
   an XOR gate configured to be input with said square-wave input signal and with a corresponding periodic output signal generated by the shock sensor and configured to output a logic XOR signal; and
   a processor configured to receive the logic XOR signal, determine a duty-cycle of said logic XOR signal, determine a phase difference based on said duty-cycle, cause said square-wave generator to adjust a frequency of said square-wave input signal, and generate said signal representing said resonance frequency of the shock sensor.

9. A method, comprising:
   filtering an output of a shock sensor with a notch filter, the filtering including:
   determining a resonance frequency of said shock sensor, the determining including:
   providing to the shock sensor a periodic input signal having a frequency in a frequency interval;
   calculating a frequency value for said periodic input signal in said frequency interval for which a phase difference between said periodic input signal and a corresponding periodic output signal of the shock sensor is minimum, the corresponding periodic output signal being an electrical response of the shock sensor to the periodic input signal being provided to the shock sensor;

generating a signal indicating that a resonance frequency has been determined and generating a signal representing said resonance frequency as a value of the frequency of said periodic input signal;

tuning said notch filter using said signal representing said resonance frequency; and filtering the output of said shock sensor using said tuned notch filter.

10. The method of claim 9, wherein calculating the frequency value includes:

comparing said phase difference with a threshold;

when said threshold is not crossed, choosing a different frequency value for said periodic input signal in said frequency interval before providing to the shock sensor the periodic input signal having the different frequency value.

11. The method of claim 9, wherein said threshold corresponds to the absolute value of said phase difference of about 45° or greater.

12. The method of claim 9, wherein said periodic input signal is a square-wave input signal.

13. The method of claim 12, wherein calculating the frequency value includes:

comparing said phase difference with a threshold;

when said threshold is not crossed, choosing a different frequency value for said periodic input signal in said frequency interval before providing to the shock sensor the periodic input signal having the different frequency value;

generating a logic XOR signal corresponding to a logic XOR between said square-wave input signal and the corresponding periodic output signal;

comparing a duty-cycle of said logic XOR signal with a corresponding level; and assessing upon said comparing whether said phase difference surpassed said threshold.

14. The method of claim 9, wherein said frequency interval is a signal bandwidth of said shock sensor.

15. The method of claim 9, further comprising:

generating a phase modulus signal representing an absolute value of the phase difference between said periodic input signal and the corresponding periodic output signal of the shock sensor; and generating a phase sign signal representing a sign of the phase difference between said periodic input signal and the corresponding periodic output signal of the shock sensor, wherein the calculating of the frequency value includes calculating the frequency value based at least in part on the phase modulus signal and the phase sign signal.

16. The method of claim 9, wherein the providing includes providing to a first terminal and a second terminal of the shock sensor the periodic input.

17. The method of claim 1, further comprising:

generating a phase modulus signal representing an absolute value of the phase difference between said periodic input signal and the corresponding periodic output signal of the shock sensor; and generating a phase sign signal representing a sign of the phase difference between said periodic input signal and the corresponding periodic output signal of the shock sensor, wherein the calculating of the frequency value includes calculating the frequency value based at least in part on the phase modulus signal and the phase sign signal.

18. The method of claim 1, wherein the providing includes providing to a first terminal and a second terminal of the shock sensor the periodic input signal.

19. The method of claim 1, further comprising:

tuning a notch filter using the signal representing said resonance frequency;

outputting from the notch filter an output signal, in response to the shock imparted to the shock sensor; and filtering with the notch filter the output signal.

20. The circuit of claim 7, further comprising:

a phase sign detection circuit configured to generate a phase sign signal representing a sign of the phase difference between said periodic input signal and the corresponding periodic output signal of the shock sensor, wherein the phase detection circuit is configured to generate a phase modulus signal representing an absolute value of the phase difference between said periodic input signal and the corresponding periodic output signal of the shock sensor, and wherein the phase check circuit is configured to calculate the frequency value based at least in part on the phase modulus signal and the phase sign signal.

21. The circuit of claim 7, further comprising:

a tunable notch filter configured to filter an output signal of the shock sensor in response to the shock imparted to the shock sensor, the notch filter being tuned using the signal representing said resonance frequency.

* * * * *